US006749581B2

(12) United States Patent
Thompson et al.

(10) Patent No.: US 6,749,581 B2
(45) Date of Patent: Jun. 15, 2004

(54) VARIABLE INFUSION RATE CATHETER

(75) Inventors: David L. Thompson, Andover, MN (US); Michael F. Mattes, Chandler; Lary R. Larson, Gold Canyon, both of AZ (US); Kenneth T. Heruth, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 219 days.

(21) Appl. No.: 09/776,436

(22) Filed: Feb. 2, 2001

(65) Prior Publication Data

US 2002/0107471 A1 Aug. 8, 2002

(51) Int. Cl.$^7$ ............................................... A61B 17/39
(52) U.S. Cl. ......................... 604/48; 604/67; 604/132
(58) Field of Search ........................ 606/545; 604/509, 604/48, 67, 132

(56) References Cited

U.S. PATENT DOCUMENTS

| | | |
|---|---|---|
| 4,447,224 A | 5/1984 | DeCant, Jr. et al. |
| 4,525,165 A | 6/1985 | Fischell |
| 4,772,263 A | 9/1988 | Dorman et al. |
| 4,871,351 A | 10/1989 | Feingold |
| 4,931,050 A | 6/1990 | Idriss |
| 5,045,064 A | 9/1991 | Idriss |
| 5,061,243 A | 10/1991 | Winchell et al. |
| 5,163,920 A | 11/1992 | Olive |
| 5,188,260 A | 2/1993 | Bettinger |

(List continued on next page.)

FOREIGN PATENT DOCUMENTS

| | | |
|---|---|---|
| EP | 0 300 552 A1 | 1/1989 |
| EP | 0 344 895 A2 | 12/1989 |
| EP | 0 564 321 A2 | 3/1993 |
| EP | 0 892 419 A2 | 1/1999 |
| EP | 0 951 916 A2 | 10/1999 |
| JP | 05220222 | 8/1993 |
| WO | WO 98/23869 | 6/1998 |

OTHER PUBLICATIONS

"microID™ 125 KhZ rfid system Design Guide", *Microchip Technology Inc.,* pp. 1–46, (Dec. 1998).
"Introducing The Microstamp Engine™", *Micron Communications, Inc.* 2 pgs., (1997).
"High Reliability Long–Term Lubricators Based On Heat–Shrink Polymers", *The Technology Partnership,* 2pgs., (Sep. 1994).
"Controlled Stepwise Motion in Polysilicon Microstructures", *Journal of Microelectromechanical Systems,* vol. 2, No. 3, pp. 106–110 (Sep. 1993).
"Digital RF/ID Enhances GPS", *Micron Communications, Inc.,* pp. 406–411 (Date Unknown).
"ALZET® osmotic Pumps, A General Description", pp. 2–5 (Date Unknown).

*Primary Examiner*—Philippe Derakshani
(74) *Attorney, Agent, or Firm*—John W. Albrecht; Stephen W. Bauer; Eric R. Waldkoetter (57) ABSTRACT

A medical device known as a catheter is configured with a variable infusion rate to deliver a therapeutic substance such as pharmaceutical compositions, genetic materials, and biologics to treat a variety of medical conditions such as pain, spasticity, cancer, and other diseases in humans and other animals. The variable infusion rate catheter provides clinician with increased flexibility, versatility, and many other improvements. The variable infusion rate catheter has a Micro Electro Mechanical System (MEMS) flow restriction with a variable infusion rate. The MEMS flow restriction is fluidly coupled to the catheter to receive therapeutic substance dispensed from a therapeutic substance delivery device and restrict the therapeutic substance flow to a desired infusion rate. Many embodiments of the variable infusion rate catheter and its methods of operation are possible.

16 Claims, 11 Drawing Sheets

U.S. PATENT DOCUMENTS

| | | |
|---|---|---|
| 5,252,962 A | 10/1993 | Urbas et al. |
| 5,368,588 A | 11/1994 | Bettinger |
| 5,423,334 A | 6/1995 | Jordan |
| 5,427,585 A | 6/1995 | Bettinger |
| 5,448,110 A | 9/1995 | Tuttle et al. |
| 5,457,447 A | 10/1995 | Ghaem et al. |
| 5,474,527 A | 12/1995 | Bettinger |
| 5,552,197 A | 9/1996 | Bettinger |
| 5,616,127 A | 4/1997 | Smith |
| 5,702,618 A | 12/1997 | Saaski et al. |
| 5,797,898 A | 8/1998 | Santini, Jr. et al. |
| 5,820,589 A | 10/1998 | Torgerson et al. |
| 5,833,603 A | 11/1998 | Kovacs et al. |
| 5,897,530 A | 4/1999 | Jackson |
| 5,944,717 A * | 8/1999 | Lee et al. .................. 606/545 |
| 6,183,441 B1 | 2/2001 | Kriesel et al. |
| 6,197,013 B1 * | 6/2001 | Reed et al. ................. 604/509 |

* cited by examiner

VARIABLE INFUSION RATE CATHETER

CROSS REFERENCE

The present application is related to the following copending application entitled "Single-Use Therapeutic Substance Delivery Device With Infusion Rate Control" by inventors Thompson et al. copending Ser. No. 09/776,471 which is not admitted as prior art with respect to the present invention by its mention in this cross reference section.

BACKGROUND OF THE INVENTION

This disclosure relates to a medical device and more particularly to a catheter used to deliver a therapeutic substance.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. One type of medical device is a catheter used to deliver a therapeutic substance.

Catheters are used to deliver a therapeutic substance from a source such as a therapeutic substance deliver device to a desired infusion site. Therapeutic substance delivery devices are also known as drug pumps and drug delivery devices can be located external to a patient or implanted within the patient. An example of a therapeutic substance delivery devices is a SynchroMed® Infusion System available from Medtronic, Inc. which includes a Model 8709 InDura catheter. Catheters can be partially inserted or implanted in a patient or fully implanted with the proximal end connected to a therapeutic substance delivery device and the distal end located near the desired infusion site. Catheter delivered therapeutic substances are typically used to treat a condition that responds to a therapeutic substance delivered directly to an infusion site in the body rather than being ingested. Catheters can be employed to treat conditions such as pain, spasticity, cancer, infections, gene abnormalities, and the like.

Catheters are typically configured with infusion rate openings fixed when the catheter is manufactured. Some catheters have a single opening at the distal end of the catheter, so the infusion rate is essential the same as the therapeutic substance deliver device infusion rate. Some catheters have more than one opening that can be configured near the catheter distal end or along the length of the catheter.

For the foregoing reasons, there is a need for a variable infusion rate catheter that permits a clinician to adjust the catheter's infusion rate before use and during use to make the catheter more versatile in treating medical conditions and have many other improvements.

SUMMARY OF THE INVENTION

The variable infusion rate catheter has a Micro Electro Mechanical System (MEMS) variable flow restriction fluidly coupled to the catheter to make the catheter more versatile and provide many other improvements. The variable infusion rate catheter permits a clinician to change the infusion rate either before the catheter is placed at an infusion site or after the catheter has been placed at an infusion site. The MEMS variable flow restriction is adjustable to vary the infusion rate from at least one catheter infusion opening. More than one MEMS variable flow restrictions can be used with a catheter to permit the catheter to have different infusion rates at different infusion openings. The catheter is coupleable to a therapeutic substance delivery device and configured to deliver therapeutic substance to a single or multiple delivery sites in a body. Many embodiments of the variable infusion rate catheter and its methods of operation are possible.

DETAILED DESCRIPTION OF THE PREFERRED EMBODIMENTS

Figure 1:
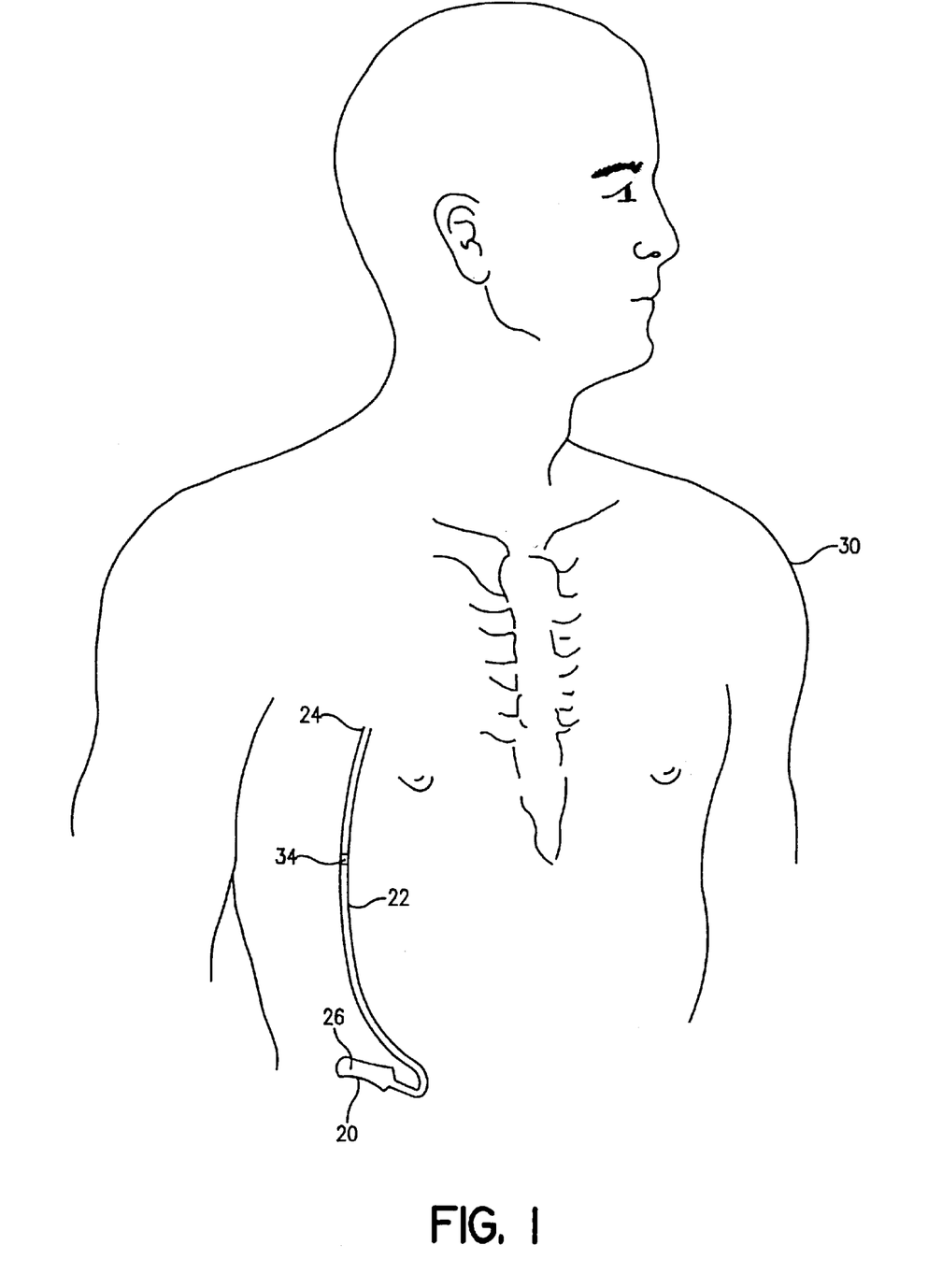
FIG. 1 shows the environment of a variable infusion rate catheter embodiment.

FIG. 1 shows the environment of a variable infusion rate catheter 22 embodiment. The catheter, typically connected to a therapeutic substance delivery device 20, can be used for a wide variety of therapies such as pain, spasticity, cancer, and other medical conditions. For implantable versions of the therapeutic substance delivery device 20, implantation is typically done by a clinician such as a surgeon in a sterile perutaneous or surgical procedure performed under local, regional, or general anesthesia. In some embodiments, before implanting the therapeutic substance delivery device 20, a catheter 22 can be implanted with the distal end 24 positioned at the desired therapeutic substance delivery site and the proximal end tunneled to the location where the therapeutic substance delivery device 20 is to be implanted. The implantable therapeutic substance delivery device 20 is generally implanted subcutaneously about 2.5 cm (1.0 inch) beneath the skin where there is sufficient subcutaneous tissue to support the implanted system. Once the therapeutic substance delivery device 20 is subcutaneously implanted into the patent the opening used to insert the therapeutic substance delivery device 20 is closed. When the therapeutic substance delivery device 20 is surgically implanted, the incision can be sutured closed.

The therapeutic substance delivery device 20 operates to infuse a therapeutic substance 26 at a programmed rate into a patient 30. The therapeutic substance 26 is a product or substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

Figure 2:
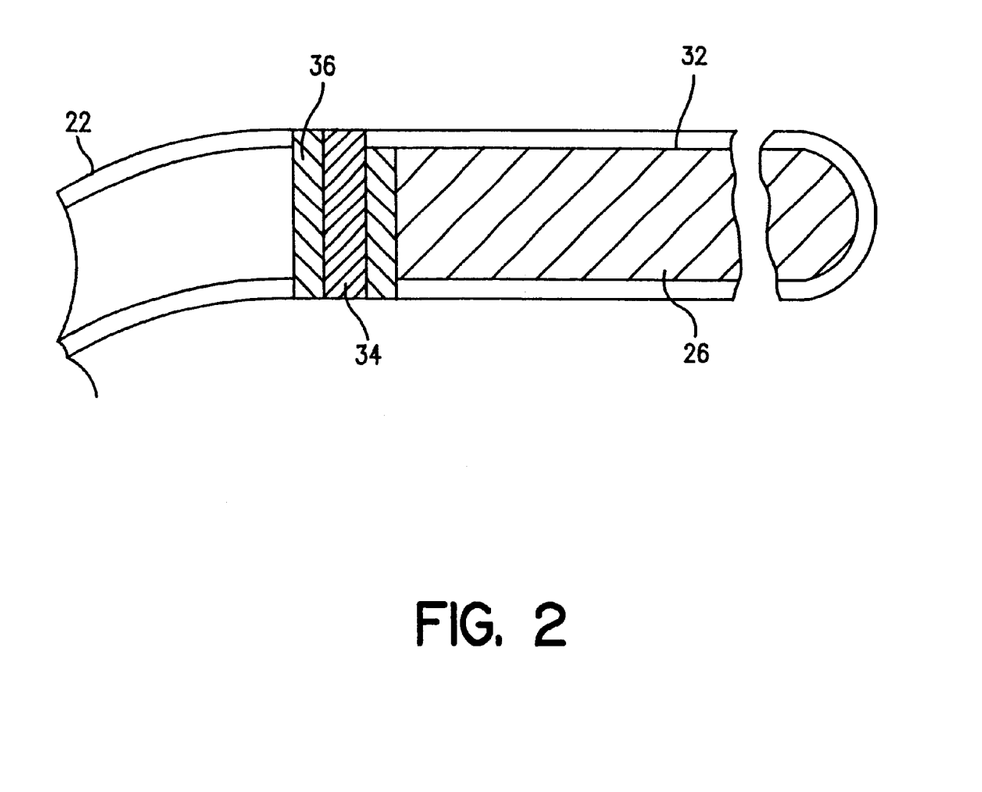
FIG. 2a shows a variable infusion rate catheter embodiment.
FIG. 2b shows another variable infusion rate catheter embodiment.
Figure 3:
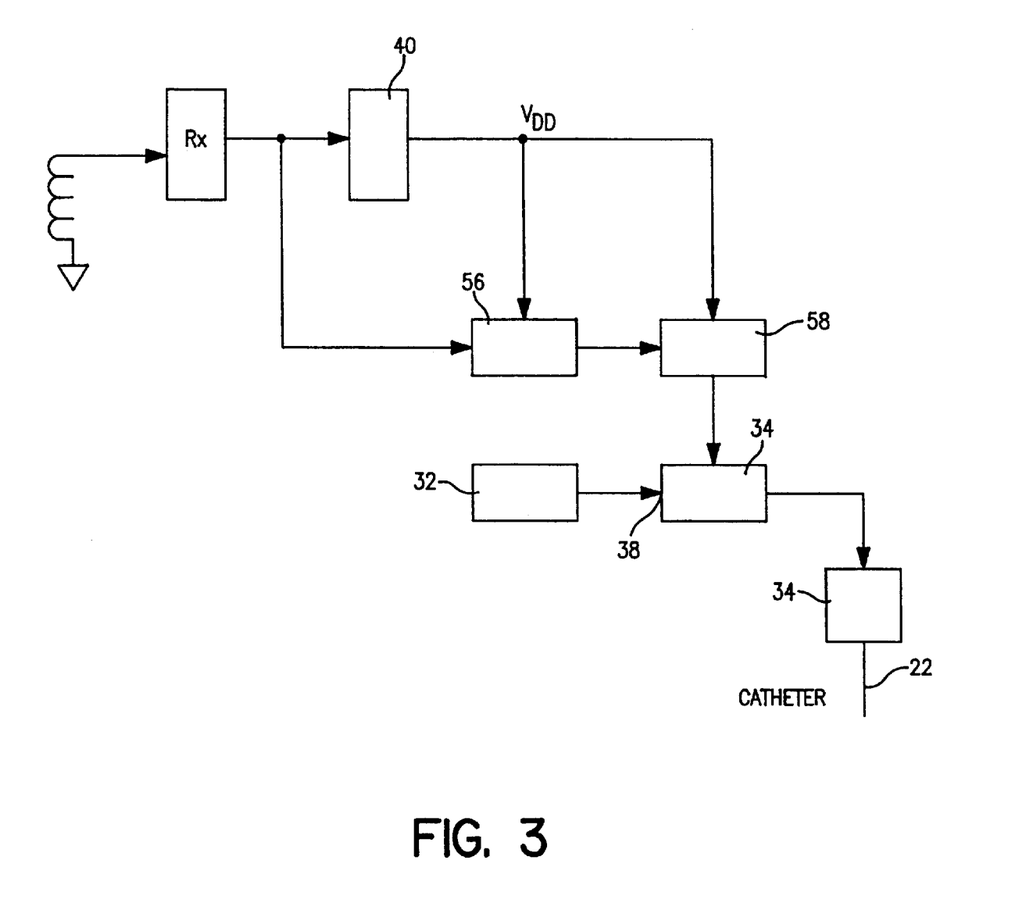
FIG. 3 shows an electrical circuit schematic for a variable infusion rate catheter with Micro Electro Mechanical System (MEMS) flow restriction embodiment.

FIGS. 2a–2b show variable infusion rate catheter embodiments, and FIG. 3 shows a schematic for a therapeutic substance delivery device 20 with a Micro Electro Mechanical System (MEMS) infusion control embodiment. In FIG. 2a, a single catheter 22 has a MEMS flow restriction 34 to adjust the infusion rate. In FIG. 2b, the catheter 22 has a first flow path 23 and a second flow path 25, and each flow path has a MEMS flow restriction, so each flow path can have an independent infusion rate.

Figure 4:
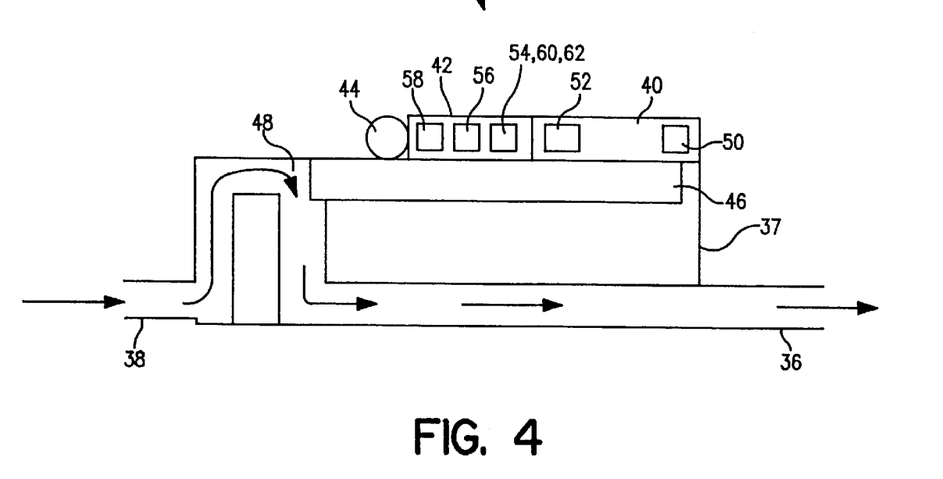
FIG. 4 shows a block diagram of a MEMS flow restriction embodiment.
Figure 5:
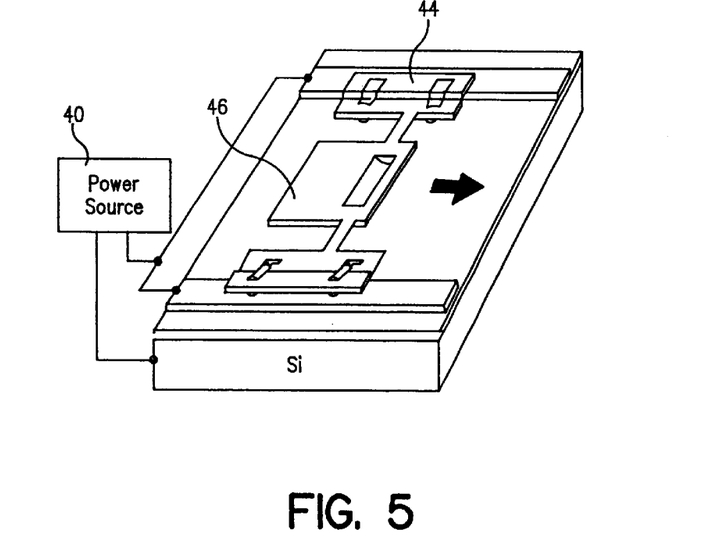
FIG. 5 shows an isometric view of a MEMS flow restriction embodiment.

FIG. 4 shows a MEMS flow restriction 34 block diagram embodiment, and FIG. 5 shows an isometric view of a MEMS flow restriction 34 embodiment. A MEMS flow restrictor 34 is fluidly coupled to the reservoir outlet 36 to receive therapeutic substance 26 dispensed from the reservoir 32 at the reservoir rate. The MEMS flow restriction 34 restricts the therapeutic substance 26 flow to an infusion rate. The MEMS flow restriction 34 is comprised of a substrate 37, a MEMS inlet 38, a MEMS outlet 36, a passive power source 40, electronics 42, an actuator 44, and a valve 46. The flow restriction 48 provides a structure to restrict therapeutic substance 26 flow that can be varied with a valve 46 such as a continuous path, a plurality of restriction outlets, and the like. MEMS 34 components such as the MEMS inlet 38 and MEMS outlet 36 can be assembled using glass frit bonding, electrostatic anodic bonding, and the like. MEMS 34 components that may contact the therapeutic substance 26 can be coated with a substance to improve chemical compatibility with the therapeutic substance and with body tissues such as titanium, platinum, gold, parylene, and the like. The MEMS substrate 37 can be cut in shape appropriate for the application such as round, rectangular, square, and the like with a laser cutter or wafer scribe saws. When configured in a round shape, the MEMS 34 is particularly well suited for use in a catheter 22 or single-use reservoir outlet 36.

The passive power source 40 is carried on the substrate 37 and comprises an antenna coil 50 and modulation circuitry 52. The passive power source 40 is capable of supplying power upon being energized by a Radio Frequency source. In one embodiment, the passive power source is operates according to Radio Frequency Identification (RFID) principals such as described in the Microchip Technology Inc., microID™ 125 kHz RFID System Design Guide (1998), U.S. Pat. No. 5,833,603 "Implantable Biosensing Transponder" by Kovacs et al., and U.S. Pat. No. 5,252,962 "System Monitoring Programmable Implantable Transponder" by Urbas et al. The RF signal is transmitted by a device such as an interrogator or a clinician's programmer configured to transmit the RF signal. The RF signal can be generated at any acceptable frequency such as 125 KHz, 13.56 MHz, 2.4 GHz, and the like. The RF signal field varies in voltage from the very near field of about 200 $V_{pp}$ to the far field of about 5 $V_{pp}$. The RF signal contacts a carrier signal at the selected frequency and a data signal modulated on this carrier signal with modulation techniques such as amplitude modulation, frequency modulation, frequency shift keying, phase modulation, phase shift keying, and the like. When the RF signal passes through the antenna coil 50, an Alternating Current (AC) voltage is generated across the antenna coil 50 and the antenna coil 50 receives the data signal. In addition to the passive power source 40, the MEMS flow restriction 34 could be configured similarly to that disclosed in U.S. Pat. No. 5,702,618 by Saaski and operated as described in Akiyama "*Controlled Stepwise Motion In Polysilicon Microstructures*" IEEE Journal of Microelectromechanical Systems, Vol. 2, No. 3 (September 1993). The MEMS flow restriction 34 can also be configured as described below.

The electronics 42 are carried on the substrate 37 and coupled to the passive power source 40. The electronic 42 include a rectifier 54, receiver circuitry 56, and control circuitry 58. The rectifier 54 rectifies the AC voltage generated across the antenna coil 50 to power the MEMS 34. The rectified power available to the MEMS 34 depends upon how the passive power source 40 is configured and can range from a voltage from less than about 2 VDC to about 10 VDC and current from less than about 5 $\mu A$ to about 50 mA. The receiver 56 is configured for the type of modulation being used to receive the data signal and produces an information signal. The control circuitry 58 converts the information signal into a control signal that is configured to operate the actuator. In some embodiments, the electronics 42 can be configured with a transmitter 60 to transmit selected information from nonvolatile memory 62 through the antenna coil 50 to the interrogator. The transmitter 62 can be a shunt transistor placed across the antenna coil 50 that is operated to cause amplitude fluctuations in the interrogator's RF carrier amplitude. The backscattered signal can be used to provide information about the MEMS 34 such as the MEMS 34 model number, MEMS 34 serial number, programmed infusion rate, and the like.

The actuator 44 is carried on the substrate and coupled to the electronics 42. The actuator 44 is a device that moves to operate the valve 46 in response to the control signal such as a stepwise rotor, a heat motor, a Direct Current (DC) motor, and the like. The heat motor contains a material that changes shape or volume in response to heat such as a memory metal, wax, and the like. In a memory metal embodiment, the memory metal such as nitanol can be formed in the shape of a bubble that changes shape in response to heat. In some embodiments, the actuator 44 can include a mechanical coupling between the actuator and the valve such as a ratchet wheel to couple the heat motor to the valve, a gear to couple the DC motor to the valve, and the like.

Figure 9A:
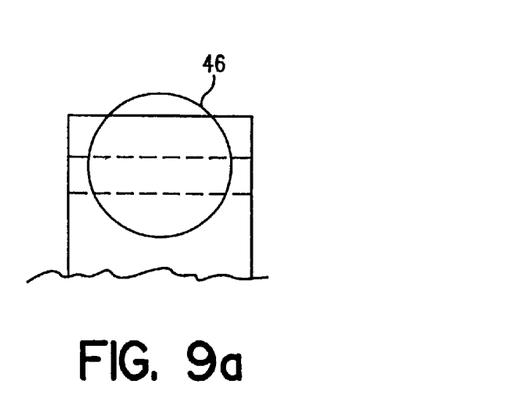
FIGS. 9a–9c show valve configurations for MEMS flow restriction embodiments; and, FIG. 10 shows a flowchart of a method for varying a catheter infusion rate.
Figure 9B:
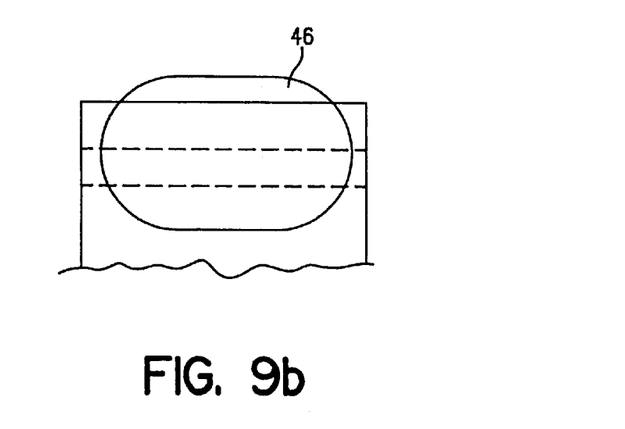
Figure 9C:
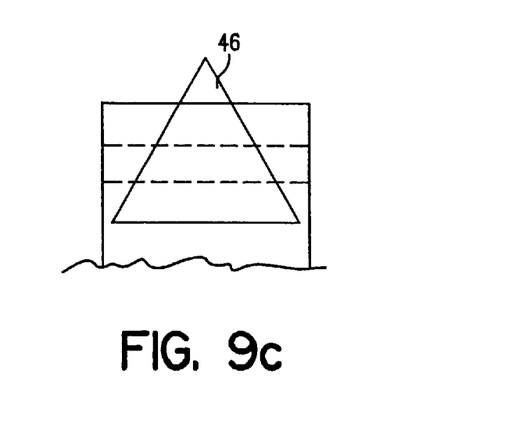

The valve 46 is moveably coupled to the substrate 37 to selectively engage the flow restriction 48. The valve 46 can take many different forms to adjust the flow restriction 48 such as a shutter, a moveable plate, a rotatable restrictor, and the like. When the valve is a moveable plate or shutter, the valve can be configured in a variety of shapes such as a circle, oval, triangle, and the like (FIGS. 9a–9c). The valve 46 is operated by the actuator 44 to selectively adjust the flow restriction 48 to create the infusion rate.

Figure 6A:
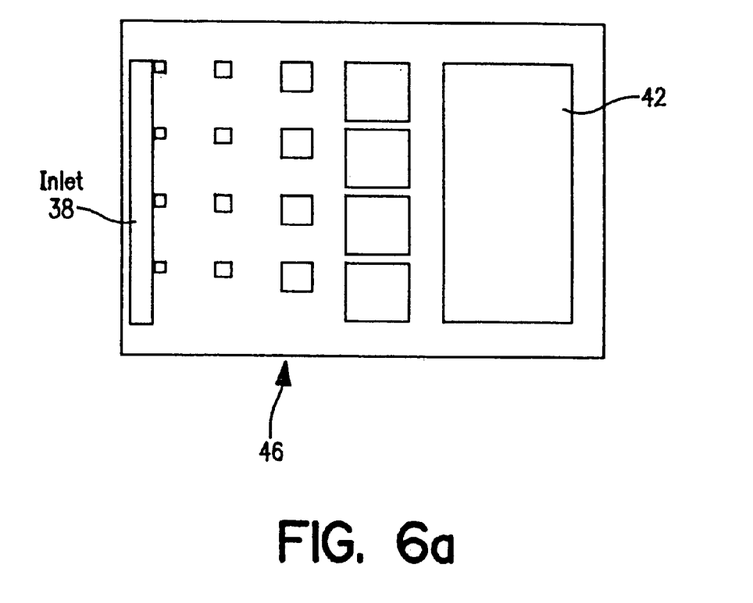
FIG. 6a shows a top view of a MEMS flow restriction having multiple outlets embodiment.
Figure 6B:
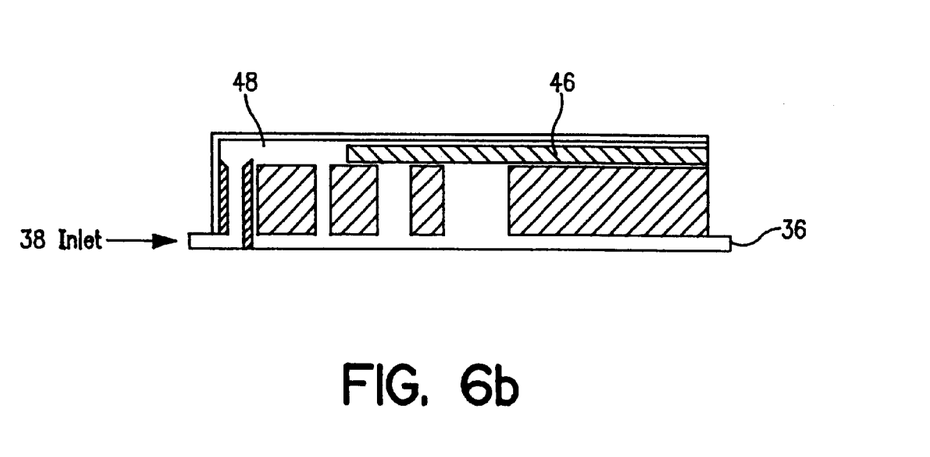
FIG. 6b shows a side view of the MEMS in FIG. 4a embodiment.
Figure 7A:
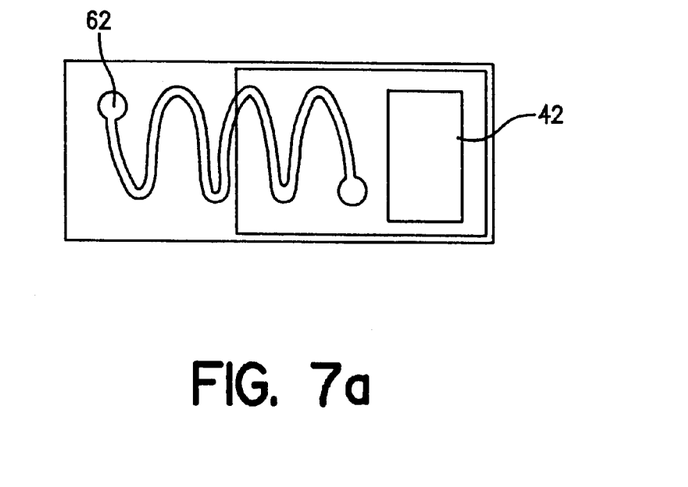
FIG. 7a shows a top view of a MEMS flow restriction having a continuous flow path embodiment.
Figure 7B:
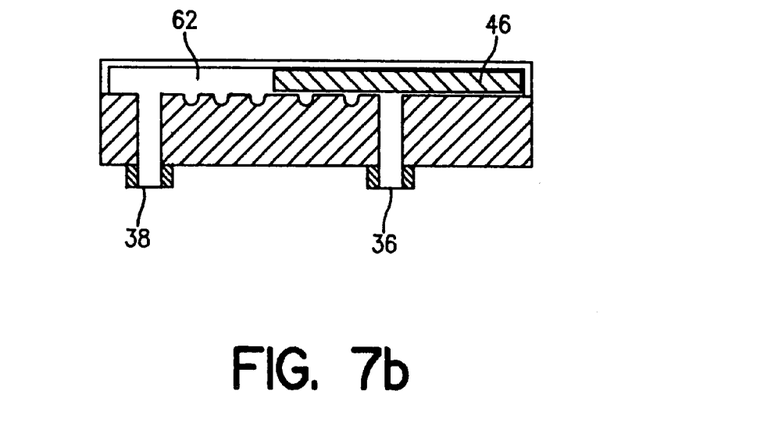
FIG. 7b shows a side view of the MEMS in FIG. 5a embodiment.
Figure 8A:
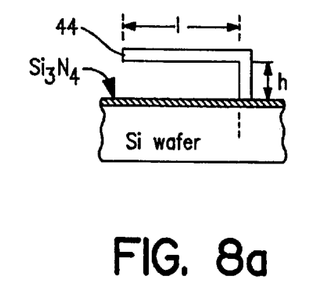
FIGS. 8a–8c show views of a stepwise actuator for a MEMS flow restriction embodiment.
Figure 8B:
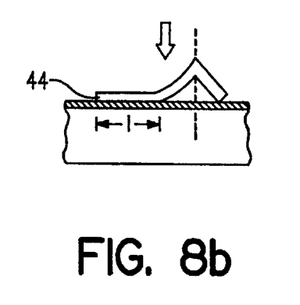
Figure 8C:
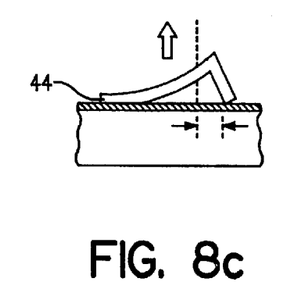
Figure 8D:
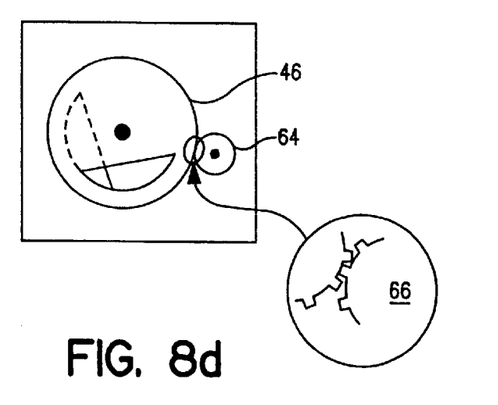
FIG. 8d shows a Direct Current (DC) motor actuator for a MEMS flow restriction embodiment.
Figure 8E:
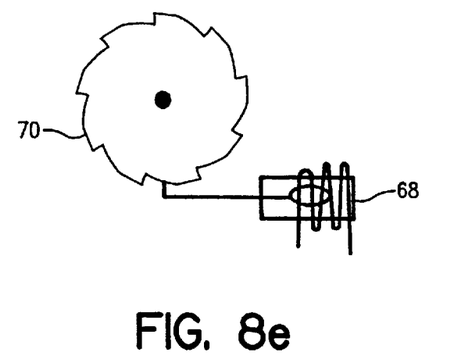
FIG. 8e shows a heat engine actuator for a MEMS flow restriction embodiment.

Many different embodiments of MEMS flow restriction 34 components are possible. FIGS. 6a–6b show an embodiment using multiple outlets that are opened, partially opened, and closed by the actuator. In another version of this embodiment, the multiple outlets are covered with a membrane. The infusion rate is programmed by the actuator 44 breaking or blowing the membrane covering selected outlets. A limitation in using membrane as the valve is that once the membrane is opened over a selected outlet that outlet cannot be closed, so reprogramming is limited to increasing the infusion rate. FIGS. 7a–7b show an embodiment of the MEMS flow restriction 34 with a continuous flow path 62. FIGS. 8a–8c show an actuator 44 embodiment using controlled stepwise motion. The stepwise motion is created by applying a voltage across the L shaped member and the substrate causing the L shaped member to be electrostatically attracted to the substrate. When the voltage is no longer applied, the L shaped member relaxes, and the L shaped member has moved forward delta x. FIG. 8d shows a DC motor 64 that can operate bi-directionally engaging a gear 66 that rotates a rotary valve 46 to adjust the infusion rate. FIG. 8e shows a heat engine 68 engaging a ratchet wheel 70 that can rotate a rotary valve 46 such as shown in FIG. 8d to adjust the infusion rate. FIGS. 9a–9c show various shapes for shutter type valves 46. The shutters can be shaped to change the infusion rate with movement in a linear or nonlinear manner.

In an alternative embodiment, a MEMS flow restriction 34 can be placed downstream from the reservoir 32 on the catheter 22 whether or not the reservoir 32 has a flow restriction 48. In another embodiment, two or more MEMS flow restrictions 34 can be placed downstream from the reservoir 32 on one or more catheters 22 whether or not the reservoir 32 has a flow restriction. When the MEMS flow restriction 34 is placed serially on a catheter 22, different infusion outlets can have different infusion rates. When more than one MEMS flow restriction 34 is placed on two or more branches of a catheter 22, the different catheter branches can have different infusion rates.

Figure 10:
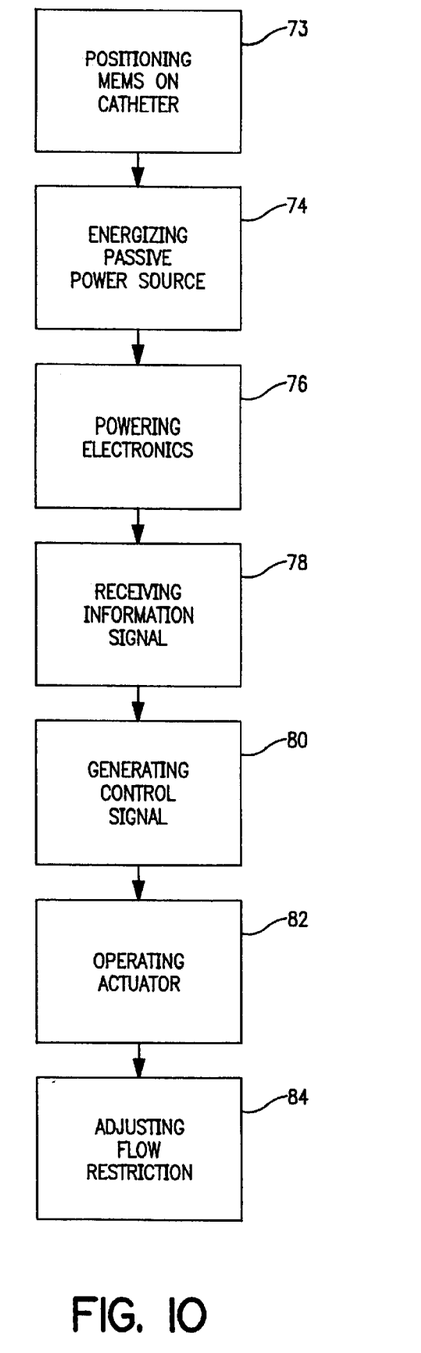
Figure 11:
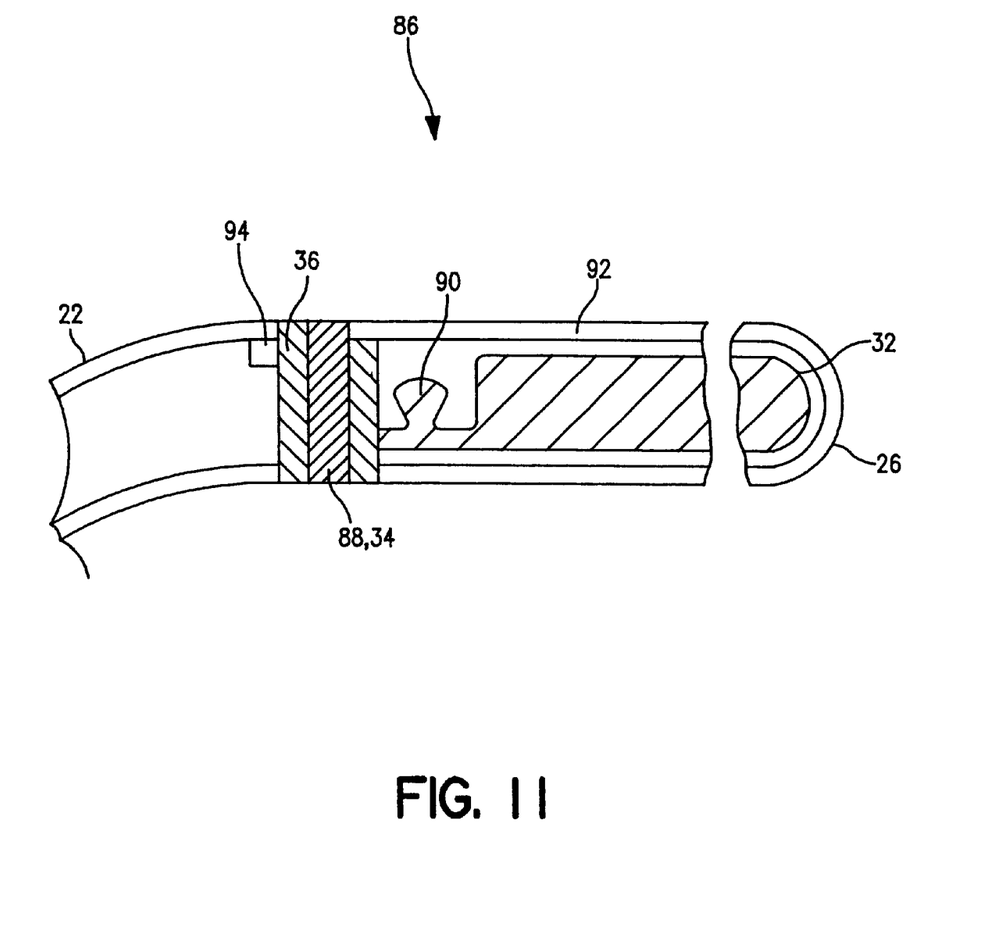
Figure 12:
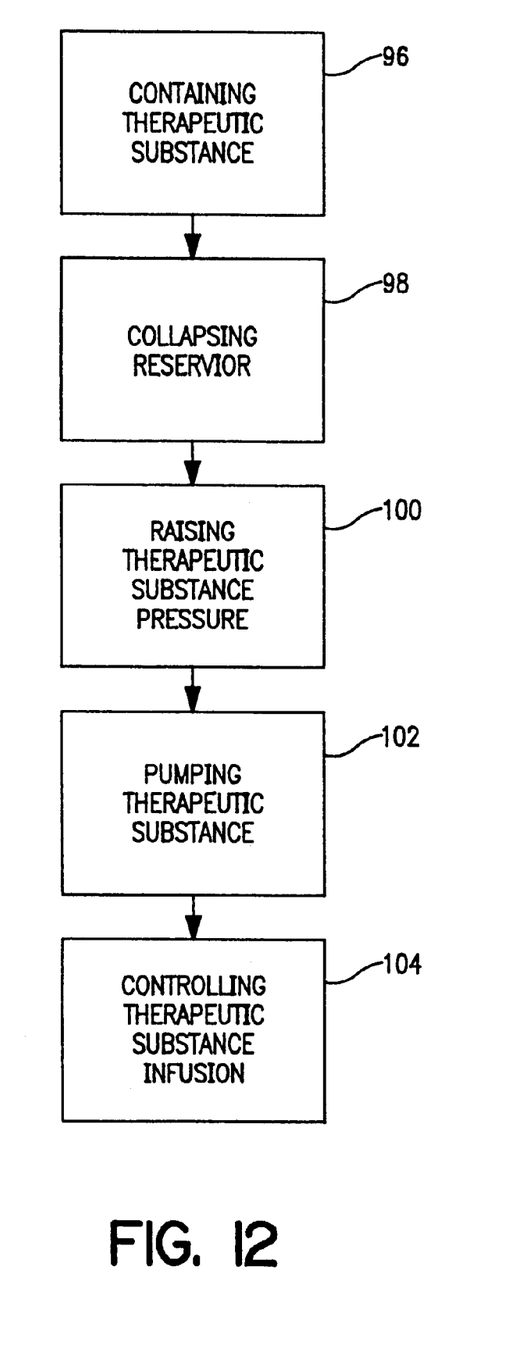

FIG. 10 shows a method for operating the MEMS flow restriction 34. The MEMS flow restriction 34 operates according to the following method. A passive power supply is energizing 74 with a radio frequency signal. The energized passive power supply powers 76 the electronics. The powered electronics receive 78 an information signal modulated on the radio frequency signal. The information signal contains at least one instruction for the MEMS flow restriction such as change the infusion rate, identify the MEMS flow restriction by model and serial number, and the like. The electronics generate 80 a control signal that is response to the information signal. The control signal is configured to drive the actuator used in the MEMS flow control embodiment. The actuator operates 82 in response to the control signal. The motion of the actuator is used to adjust 84 the valve to adjust the flow restriction to an infusion rate. In some embodiments, the method can also include transmitting a status signal with the electronics such as the currently programmed infusion rate.

FIG. 10 shows a method for operating the MEMS flow restriction used with a variable infusion rate catheter. The MEMS flow restriction operates according to the following method. A MEMS flow restriction 34 is positioned 73 in the catheter. A passive power supply is energizing 74 with a radio frequency signal. The energized passive power supply powers 76 the electronics. The powered electronics receive 78 an information signal modulated on the radio frequency signal. The information signal contains at least one instruction for the MEMS flow restriction such as change the infusion rate, identify the MEMS flow restriction by model and serial number, and the like. The electronics generate 80 a control signal that is response to the information signal. The control signal is configured to drive the actuator used in the MEMS flow control embodiment. The actuator operates 82 in response to the control signal. The motion of the actuator is used to adjust 84 the valve to adjust the flow restriction to an infusion rate. In some embodiments, the method can also include transmitting a status signal with the electronics such as the currently programmed infusion rate.

The catheter with a Micro Electo Mechanical System (MEMS) variable infusion rate comprises a catheter, and a MEMS variable flow restriction. The catheter is coupleable to a therapeutic substance delivery device. The catheter configured to deliver therapeutic substance to one or more delivery sites in a body. The MEMS variable flow restriction is fluidly coupled to the catheter. The MEMS variable flow restriction is adjustable to vary the infusion rate from at least one catheter infusion opening.

The catheter 22 can be percutaneously inserted into a patient, and the catheter 22 can be programmed after implantation. The catheter 22 serves as a means for therapeutic substance 26 delivery to a delivery site. In one embodiment, the catheter 22 has at least a first flow path 23 and a second flow path 25. The first flow path 23 and the second flow path 25 each have a MEMS variable flow restriction 34 capable of providing a first infusion rate and a second infusion rate.

Thus, embodiments of the variable infusion rate catheter are disclosed to increase versatility, increase flexibility, and provide many other improvements. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A variable infusion rate catheter, comprising:
    a catheter coupleable to a therapeutic substance delivery device, the catheter configured to deliver therapeutic substance to a delivery site in a body; and,
    a Micro Electro Mechanical System (MEMS) variable flow restriction fluidly coupled to the catheter, the MEMS variable flow restriction adjustable to vary the infusion rate from at least one catheter infusion opening.

2. The catheter as in claim 1 wherein the catheter is configured to be percutaneously inserted into a patient.

3. The catheter as in claim 1 wherein the catheter is configured to be programmed after implantation.

4. The variable infusion rate catheter as in claim 1 wherein the MEMS variable flow restriction further comprises,
    a substrate having a therapeutic substance flow path with a therapeutic substance input, a flow restriction, and a therapeutic substance output;
    a passive power source carried on the substrate, the passive power source capable of supplying power upon being energized by a radio frequency source;
    electronics carried on the substrate and coupled to the passive power supply, the electronics generating a control signal;

an actuator carried on the substrate and coupled to the control electronics, the actuator moving in response to the control signal; and, a valve moveably coupled to the substrate to selectively engage the flow restriction, the valve operated by the actuator to selectively adjust the flow restriction to for an infusion rate.

5. The catheter as in claim 1 wherein the catheter has a proximal end and a distal end, the distal end having at least a first flow path and a second flow path, the first flow path and the second flow path each having a MEMS variable flow restriction capable of providing a first infusion rate and a second infusion rate.

6. A variable infusion rate catheter, comprising:

means for therapeutic substance delivery to deliver therapeutic substance to a delivery site; and, means for variable flow restriction fluidly coupled to the means for therapeutic substance delivery, the means for variable flow restriction including a Micro Electro Mechanical System (MEMS) variable flow restriction adjustable to vary the infusion rate from at least one catheter infusion opening.

7. A method for varying a catheter infusion rate, comprising:

positioning a MEMS variable flow control on a catheter;

energizing a passive power supply with a radio frequency signal;

powering electronics with the passive power supply;

receiving an information signal modulated on the radio frequency signal with the electronics;

generating a control signal that is responsive to the information signal with the electronics;

operating an actuator in response to the control signal; and, moving a valve with the actuator to adjust the flow restriction for an infusion rate.

8. The method as in claim 1, further comprising, supplying the catheter with therapeutic substance; and, infusing therapeutic substance from the catheter at the programmed infusion rate.

9. A Micro Electo Mechanical System (MEMS) variable flow restriction for a catheter, comprising:

a substrate having a drug flow path with drug input, a flow restriction, and a drug output;

a passive power source carried on the substrate, the passive power source capable of supplying power upon being energized by a radio frequency source;

electronics carried on the substrate and coupled to the passive power supply, the electronics generating a control signal;

an actuator carried on the substrate and coupled to the electronics, the actuator moving in response to the control signal; and, a valve moveably coupled to the substrate to selectively engage the flow restriction, the valve operated by the actuator to selectively adjust the flow restriction to modulate the flow through the drug flow path.

10. The MEMS flow restrictor as in claim 9 wherein the control electronics include nonvolatile memory.

11. The MEMS flow restrictor as in claim 9 wherein the actuator is a D.C. motor coupled to the valve with a gear.

12. The MEMS flow restrictor as in claim 9 wherein the actuator is a heat motor coupled to the valve with a ratchet wheel.

13. The MEMS flow restrictor as in claim 9 wherein the actuator is a stepwise rotor coupled to the valve.

14. The MEMS flow restrictor as in claim 9 wherein the flow restriction is a continuous path.

15. The MEMS flow restrictor as in claim 9 wherein the flow restriction is a plurality of restriction outlets selectable by the valve.

16. A Micro Electo Mechanical System (MEMS) flow restriction for a catheter, comprising:

means for therapeutic substance flow having a therapeutic substance input, a flow restriction, and a therapeutic substance output;

means for power carried on the means for therapeutic substance flow, the means for power capable of supplying power upon being energized by a radio frequency source;

means for programming to store flow restriction program;

means for electronics control to receive the flow restriction program and generate a control signal;

means for actuation to create motion in response to the control signal; and, means for valving to adjust therapeutic substance flow through the flow restriction moveably coupled to the substrate to selectively engage the flow restriction, the shutter operated by the actuator to selectively adjust the flow restriction to modulate the flow through the drug flow path.

\* \* \* \* \*

UNITED STATES PATENT AND TRADEMARK OFFICE
CERTIFICATE OF CORRECTION

PATENT NO. : 6,749,581 B2 Page 1 of 1
DATED : June 15, 2004
INVENTOR(S) : Thompson et al.

It is certified that error appears in the above-identified patent and that said Letters Patent is hereby corrected as shown below:

<u>Column 7,</u>
Line 39, reads "in claim1,…" should read -- …in claim 7… --.

Signed and Sealed this

Sixth Day of December, 2005

JON W. DUDAS
*Director of the United States Patent and Trademark Office*